US00PP30704P3

(12) United States Plant Patent
Cain

(10) Patent No.: US PP30,704 P3
(45) Date of Patent: Jul. 16, 2019

(54) SWEET CHERRY TREE NAMED 'IFG CHER-FOUR'

(50) Latin Name: *Prunus avium*
Varietal Denomination: IFG Cher-four

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 172 days.

(21) Appl. No.: 15/530,648

(22) Filed: Feb. 15, 2017

(65) Prior Publication Data

US 2018/0235123 P1 Aug. 16, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445; A01H 5/08
See application file for complete search history.

*Primary Examiner* — Keith O. Robinson

(57) ABSTRACT

This invention is a new and distinct sweet cherry tree denominated 'IFG Cher-four'. The new sweet cherry tree is characterized by producing medium size blushed fruits having flat-round shape. Fruits ripen early, about Apr. 26, 2014 in Delano Calif. The 'IFG Cher-four' has medium firm, medium acid fruit with a good cherry flavor. Fruits are tolerant of rain induced cracking. The sweet cherry tree has a medium low chilling requirement, about 300 to 400 chill hours.

1 Drawing Sheet

Latin name of the genus and species claimed: *Prunus avium.*

Variety denomination: 'IFG Cher-four'.

BACKGROUND OF THE INVENTION

The new and distinct sweet cherry tree described and claimed herein originated from open pollinated seeds of fruits of an early ripening unidentified female parent located in Bakersfield, Kern County, Calif. collected in May 2001. The male parent is unknown. The seeds were stratified, germinated and the resulting 540 seedlings were planted in a field near Delano, Kern County, Calif. in April 2002. The present variety of sweet cherry tree was selected as a single plant in May 2005 and was first asexually propagated in January 2006 by grafting onto *Prunus mahalab* rootstock. These propagules were found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-four' is characterized by producing medium size blushed fruits having flat-round shape. The 'IFG Cher-four' has medium firm, medium acid fruit with a good cherry flavor ripening in early season. Fruits are tolerant of rain induced cracking. The tree has a low chilling requirement; about 300 to 400 chill hours, which is lower than the 'Brooks' (U.S. Plant Pat. No. 6,676); about 400 to 500 chill hours, and 'Rainier' (non-patented); about 700 chill hours, varieties. It produces fewer doubled and spurred fruits as compared to the 'Brooks' and 'Rainier' varieties in high summer temperature regions such as the Southern San Joaquin Valley of California. Fruits of 'IFG Cher-four' have medium long, medium thick stems that remain attached and stay green during storage and shipping.

In comparison to the 'Rainier' variety, which is the major blush variety grown in the USA, the present variety ripens about fourteen to eighteen days earlier. The tree growth is less vigorous than 'Rainier' and the leaves are more upwardly curled with slightly wavier margins. In comparison to its female parent, the present variety has fruits that have yellow flesh and yellow skin covered with a bright red blush over 50 to 80 percent of its surface as opposed to red flesh and skin color of the female parent.

BRIEF DESCRIPTION OF THE DRAWING

The accompanying photographic drawing in FIG. 1 illustrates in full color 'IFG Cher-four', taken from an 8-year old tree. The photograph was taken outdoors with indirect lighting. The colors are as nearly true as is reasonably possible in a color representation of this type. An actively growing shoot tip collected at harvest can be seen in the upper portion of the drawing. Typical nature fruit and fruit in cross-section are displayed on the lower half of the drawing. Typical cleaned and dried fruit pits are displayed on the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to an 'IFG Cher-four' plant growing in the vicinity of Delano, Kern County, Calif. during 2013 and 2014, and is believed to apply to plants of the variety grown under similar conditions of soil and climate elsewhere:

TREE

General:

*Age.*—8 yrs. old.
*Height.*—2.7 M when pruned.
*Width.*—3.3 M when pruned.
*Vigor.*—Medium to low.
*Density of foliage.*—Dense.
*Form.*—Spreading.
*Branching.*—Strong.
*Root stock.*—*Prunus mahalab.*
*Resistance to.*—Insects: Average typical of *Prunus avium* species. Diseases: Average typical of *Prunus avium* species.
*Chilling requirements.*—Low.
*Graft compatibility.*—Good: produces compatible graft unions with *Prunus avium*, 'Mazzard' seedlings (non-patented) and *Prunus mahaleb* seedlings (non-patented).

Trunk:

*Trunk diameter of* 8-*year old trees,* 30 *cm above the soil line.*—24.3 cm.
*Lenticel size.*—Small.
*Lenticel dimensions.*—Length: About 0.5 cm. Width: About 0.3 cm.
*Lenticel shape.*—Elliptical shape oriented horizontally.
*Lenticel color.*—The following colors were observed: Greyed-green:198D and Grey-brown: 199C.
*Trunk surface texture.*—Smooth to slightly rough.
*Outer bark color.*—Greyed-orange: 175A.

BRANCHES 1-year old wood:

*Vertical top growth length.*—Long: About 153 cm.
*Horizontal growth length.*—Medium long: About 73.5 cm.
*Diameter.*—Vertical growth: 1.6 cm. Horizontal growth: 0.9 cm.
*Internode length.*—About 4.4 cm.
*Number of lenticels.*—Few to medium: About 6 lenticels per linear cm.
*Lenticel size.*—Small.
*Lenticel dimensions.*—Length: About 0.1 cm. Width: About 0.1 cm.
*Lenticel shape.*—Round.
*Bark color.*—The following colors were observed: Grey-brown: 199A and Greyed-orange: 172A.

2-year old wood:

*Length.*—Medium: About 29.5 cm.
*Diameter.*—About 1.1 cm.
*Internode length.*—About 3.9 cm.
*Number of lenticels.*—About 5 lenticels per linear cm.
*Lenticel dimensions.*—Length; About 0.2 cm. Width; About 0.1 cm.
*Lenticel shape.*—Elliptical shape oriented horizontally.
*Bark color.*—The following colors were observed: Greyed-orange: 177A and Greyed-green: 197A.

BUDS

Vegetative buds:

*Shape.*—Oval.
*Vegetative bud dimensions.*—Length: About 1.8 cm. Width: About 0.3 cm.
*Vegetative bud burst.*—Feb. 10, 2014.

Flower buds:

*Flower bud dimensions.*—Length: About 1.1 cm. Width: About 0.3 cm.
*Shape.*—Oval.
*Placement.*—Mostly at bud positions 1 to 8 on 1-year wood.
*Average number of flower buds on first year wood.*—6.
*Number of flower buds per spur on second year wood.*—2 to 4. Average: About 3.
*Color.*—Greyed-orange: 177A.
*Flower bud burst.*—Feb. 14, 2014.

LEAVES

Mature leaves:

*Leaf dimensions.*—Length: About 15 cm. Width: About 6.4 cm.
*Leaf shape.*—Elongated ovate: Asymmetric on both sides of central axis.
*Shape of tip.*—Acuminate: broadly.
*Shape of base.*—Rounded.
*Margin.*—Serrated: regular.
*Leaf profile.*—Involute.

Upper surface:

*Upper surface pubescence.*—None.
*Upper leaf surface color.*—Green: 137A.
*Surface texture.*—Smooth.

Lower surface:

*Lower surface pubescence.*—Sparse to medium.
*Lower leaf surface color.*—Yellow-green: 146B.

Petiole:

*Petiole dimensions.*—Length: About 3.1 cm. Width: About 0.2 cm.
*Upper surface of petiole color.*—The following colors were observed: Greyed-red: 178A and Greyed-orange: 174A.
*Lower surface of petiole color.*—Yellow-green: 145C.
*Petiole groove.*—Medium: Approximately 0.8 mm.
*Petiole pubescence.*—Medium: only on upper surface.
*Venation.*—Arcuate.
*Vein color.*—Yellow-green: 145C.

Glands:

*Number of glands.*—1 to 4.

*Gland dimensions.*—Length: About 0.23 cm. Width; About 0.16 cm.

*Gland shape.*—Mixed globose and reniform.

*Gland location.*—On petiole.

*Gland color.*—The following colors were observed: Greyed-purple: 187B and Greyed-red: 180A.

*Leaf stipule.*—Not present.

Flowers:

*Blooming period.*—Very early.

*Blooming dates.*—First Bloom: Feb. 20, 2014. Full Bloom: Mar. 2, 2014.

*Number of flowers per cluster.*—2 to 3. Average: About 3.

*Corolla.*—Composed of unfused petals, somewhat overlapping.

*Corolla diameter.*—About 3.6 cm.

*Petal number.*—5.

*Petal length.*—About 1.5 cm.

*Petal width.*—About 1.3 cm.

*Margin waviness.*—Weak.

*Division of upper margin.*—Notched.

*Color of petal upper surface.*—The following colors were observed: White: 155B and D.

*Color of petal lower surface.*—The following colors were observed: White: 155C and D.

*Peduncle.*—Length: About 3.8 cm. Width: About 0.2 cm.

*Peduncle color.*—The following colors were observed: Yellow-green: 144A and B.

*Number of sepals.*—5.

*Sepal length.*—About 0.7 cm.

*Sepal width.*—About 0.4 cm.

*Sepal shape.*—Triangular.

*Sepal color.*—Upper surface: The following colors were observed: Green: 143A and B and Yellow-green: 144A and B. Lower surface: Purple: N79.

*Filament.*—Length: About 0.5 to 1.4 cm. Width: About 0.2 mm.

*Filament color.*—White: N155B.

*Anther color.*—Yellow-orange: 22A.

*Pollen color.*—Yellow-orange: 17D.

*Pollen production.*—Medium.

*Self-compatibility of flowers.*—Self-incompatible.

*Flower compatibility group.*—S1S6.

FRUIT

General:

*Ripening period.*—Early: Approximately: Apr. 26, 2014.

*Use.*—Fresh market.

*Keeping quality.*—Average.

*% Titratable acidity.*—About 0.82%.

*Refractometer test.*—Soluble solids: Brix — About 18.2.

*Firmtech II (g/mm).*—About 365.

*Flavor.*—Good, medium acidity.

*Juice color.*—Yellow-orange: 22A.

*Juice amount.*—Intermediate.

*Eating quality.*—Good.

Stem:

*Stem.*—Length: About 3.8 cm. Width: About 0.2 cm.

*Stem color.*—The following colors were observed: Yellow-green: 144A and B.

*Stem cavity.*—Medium.

*Stem retention during storage.*—Very good.

*Stem storage quality.*—Good.

Berry:

*Uniformity of size.*—Uniform.

*Shape.*—Flat-round.

*Fruit weight.*—About 10.5 gm.

*Apical diameter.*—About 2.5 cm.

*Diameter transversely across suture.*—About 2.1 cm.

*Diameter at right angle to suture plane.*—About 2.6 cm.

*Suture.*—None.

*Percent of excessively deep or split sutures.*—About 0%.

*Doubles.*—About 0%.

Skin:

*Texture.*—Smooth, tender.

*Skin color.*—The following colors were observed: Yellow-orange: 15D and Red: 45A.

*Tendency to tip crack.*—Not susceptible.

*Tendency to stem cavity crack.*—Not susceptible.

*Tendency to suture crack.*—Not susceptible.

Flesh:

*Texture.*—Intermediate.

*Color.*—The following colors were observed: Red: 46A and B and C and Yellow: 11A and B.

Stone:

*Shape.*—Oblong.

*Length.*—About 1.3 cm.

*Width transversely across suture.*—About 1.0 cm.

*Width at right angle to suture plane.*—About 0.7 cm.

*Type.*—Clingstone.

*Surface texture.*—Slightly rough.

*Stone color when dry.*—Orange-white: 158A.

*Tendency to split.*—None.

*Base.*—Rounded.

*Apex.*—Rounded.

*Ventral edge.*—Prominent suture protruding somewhat beyond the horizontal plane of the base of the stone, subtended by two ridges extending from base to apex.

*Dorsal edge.*—Narrow ridge from base to apex.

What is claimed:

1. A new and distinct variety of sweet cherry tree as herein illustrated and described.

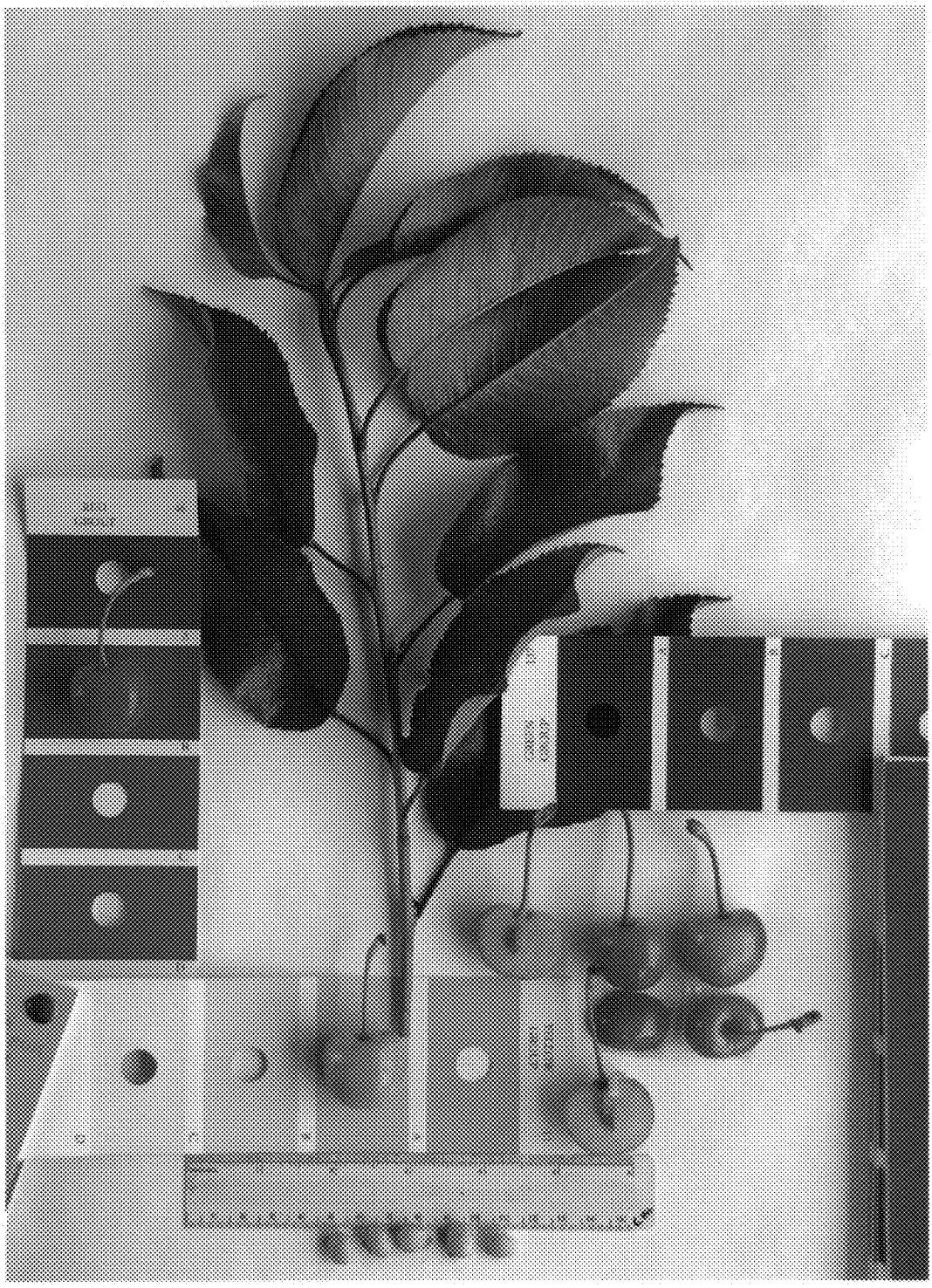

* * * * *